United States Patent
Madan et al.

(10) Patent No.: US 12,414,979 B2
(45) Date of Patent: Sep. 16, 2025

(54) COMPOSITIONS AND METHODS FOR TREATING SJOGREN'S SYNDROME

(71) Applicants: Interlude Biopharma Co., Miami, FL (US); Oklahoma Medical Research Foundation, Oklahoma City, OK (US)

(72) Inventors: Jay P. Madan, Raleigh, NC (US); Kathy L. Sivils, Oklahoma City, OK (US); Umesh Deshmukh, Oklahoma City, OK (US); Balasingham Radhakrishnan, Raleigh, NC (US); Kendyle Kennsengten, Raleigh, NC (US); Harini Bagavant, Oklahoma City, OK (US)

(73) Assignees: Interlude Biopharma Co., Miami, FL (US); Oklahoma Medical Research Foundation, Oklahoma City, OK (US)

( * ) Notice: Subject to any disclaimer, the term of this patent is extended or adjusted under 35 U.S.C. 154(b) by 863 days.

(21) Appl. No.: 17/517,886

(22) Filed: Nov. 3, 2021

(65) Prior Publication Data
US 2022/0047668 A1    Feb. 17, 2022

Related U.S. Application Data

(63) Continuation of application No. PCT/US2020/031567, filed on May 6, 2020.

(60) Provisional application No. 62/843,823, filed on May 6, 2019.

(51) Int. Cl.
| | | |
|---|---|---|
| *A61K 38/00* | (2006.01) | |
| *A61K 31/196* | (2006.01) | |
| *A61K 31/606* | (2006.01) | |
| *A61K 38/08* | (2019.01) | |
| *A61P 1/02* | (2006.01) | |

(52) U.S. Cl.
CPC ........... *A61K 38/08* (2013.01); *A61K 31/196* (2013.01); *A61K 31/606* (2013.01); *A61P 1/02* (2018.01)

(58) Field of Classification Search
CPC .............. A61K 2300/00; A61K 31/196; A61K 31/606; A61K 38/08; A61K 45/06; A61K 9/0048; A61P 1/02; A61P 37/00
See application file for complete search history.

(56) References Cited

U.S. PATENT DOCUMENTS

| | | | | |
|---|---|---|---|---|
| 5,688,765 | A | * | 11/1997 | Sullivan ................. A61P 27/02 514/8.9 |
| 2006/0062787 | A1 | | 3/2006 | Hitraya |
| 2007/0254831 | A1 | | 11/2007 | Mezo et al. |
| 2015/0038905 | A1 | | 2/2015 | Andino et al. |
| 2015/0164978 | A1 | | 6/2015 | Paterson et al. |
| 2016/0022760 | A1 | | 1/2016 | Perrow et al. |
| 2018/0028516 | A1 | * | 2/2018 | Zarnitsyn ................. A61P 7/02 |
| 2021/0030814 | A1 | * | 2/2021 | Madan ..................... C12N 1/20 |

FOREIGN PATENT DOCUMENTS

| | | |
|---|---|---|
| WO | 2017109087 A1 | 6/2017 |
| WO | 2019165345 A1 | 8/2019 |

OTHER PUBLICATIONS

Somani et al. (JIAOMR Jan.-Mar. 2011;23(1):61-64). Sjögren's Syndrome: A Review. (Year: 2011).*
PCT International Patent Application No. PCT/US2020/031567, International Search Report and Written Opinion mailed Aug. 6, 2020, 11 pages.

* cited by examiner

*Primary Examiner* — Lianko G Garyu
*Assistant Examiner* — Mercy H Sabila
(74) *Attorney, Agent, or Firm* — Morgan, Lewis & Bockius LLP (57) ABSTRACT

The present invention provides compositions and methods for treating Sjogren's syndrome (SS), including primary or secondary SS, as well as methods for preventing clinical disease in patients at risk of developing clinical SS. In various embodiments, the invention relates to administering a regimen of larazotide (or derivative) and/or 4-APAA compounds or 5-ASA compounds (e.g., 5-ASA, 4-ASA, 4-Ac APAA, and 4-APAA) to a patient in need thereof.

10 Claims, 4 Drawing Sheets

Specification includes a Sequence Listing.

COMPOSITIONS AND METHODS FOR TREATING SJOGREN'S SYNDROME

CROSS-REFERENCE TO RELATED APPLICATIONS

This application claims the benefit of U.S. Provisional Application No. 62/843,823, filed May 6, 2019, the entire contents of which are hereby incorporated by reference in their entirety.

FIELD OF THE INVENTION

The present invention provides compositions and methods for treating or preventing symptoms and/or progression of Sjogren's syndrome, including associated inflammatory symptoms.

DESCRIPTION OF THE TEXT FILE SUBMITTED ELECTRONICALLY

The content of the text file submitted electronically herewith is incorporated herein by reference in their entirety: A computer readable format copy of the Sequence Listing (Filename: "INN-011PC_ST25.txt"; Date created: Apr. 23, 2020; File size: 503 bytes).

BACKGROUND

Sjogren's syndrome (SS) refers to autoimmune conditions in which the moisture-producing glands of the body are affected, resulting in the development of, for example, dry mouth, dry eyes, and/or dry skin, as well as other symptoms such as a chronic cough, numbness of extremities, as well as pain and fatigue. The condition is characterized by lymphocyte infiltration within the glands, and the presence of autoantibodies. For example, lymphocytic infiltrates damage ductal and acinar epithelial cells, resulting in glandular dysfunction. Baker OJ, *Tight Junctions in Salivary Epithelium, J. of Biomedicine and Biotechnology* Volume 2010.

Sjogren's syndrome can occur independently of other health problems (primary Sjogren's syndrome) or in association with another autoimmune or connective tissue disorder (secondary Sjogren's syndrome). The inflammation resulting from SS progressively damages glands.

Treatment of Sjogren's syndrome is limited to local amelioration of symptoms and/or systemic anti-inflammatory agents.

There is a need for pharmaceutical compositions and methods for treating Sjogren's syndrome and associated conditions, including treatments that reduce or prevent symptoms of the condition, slow or stop progression of the disease, and/or prevent or delay onset.

SUMMARY OF THE INVENTION

The present invention provides compositions and methods for treating a patient having or at risk of developing Sjogren's syndrome, including primary or secondary SS. In various embodiments, the invention relates to administering a regimen of larazotide (or derivative thereof) and/or one or more anti-inflammatory compounds, such as 4-APAA compounds or 5-ASA compounds, to a patient in need thereof. The anti-inflammatory compounds include, but are not limited to, 5-Aminosalicylic acid (5-ASA), 4-Aminosalicylic acid (4-ASA), 4-acetylamino phenyl acetic acid (4-Ac APAA) and 4-aminophenylacetic acid (4-APAA). The larazotide or derivative and/or 4-APAA compounds or 5-ASA compounds may be administered locally to affected tissues (e.g., tissues comprising affected exocrine glands), or in some embodiments, to the small or large intestine to improve and/or restore GI tight junction integrity. In some embodiments, the larazotide composition is administered systemically. In some embodiments, routine hygiene with the local or topical compositions described herein promotes and/or restores tight junction integrity of exocrine glands, leading to reduced glandular inflammation and lymphocyte infiltration.

Larazotide is a peptide agent that promotes and/or restores tight junction integrity, including in the GI tract and other tissues. Larazotide has the amino acid sequence: Gly Gly Val Leu Val Gln Pro Gly (SEQ ID NO: 1), and can be formulated for local application to affected tissues or for targeted release in selected portions of the GI (e.g., small intestine and/or large intestine).

In some embodiments the patient does not have a clinical diagnosis of SS, but displays one or more symptoms or markers of the condition, such as dry eye syndrome, dry mouth (e.g., xerostomia), and/or dry skin, and in some embodiments, the presence of at least one other autoimmune condition. In some embodiments, the patient is positive for at least one autoantibody associated with SS. In these embodiments, the method can reduce symptoms, and/or slow progression of the condition, including slowing the progressive loss of glandular function.

In some embodiments, the patient has a clinical diagnosis of SS, which may be primary or secondary SS. In some embodiments, the larazotide regimen administered with or without the 4-APAA compounds or 5-ASA compounds reduces symptoms of SS in patients with severe or moderate disease including localized inflammatory symptoms, and in some embodiments, the invention stops or slows progressive loss of glandular function.

In some embodiments, the subject displays symptoms of intestinal inflammation, which can be clinical inflammatory bowel disease (IBD) or subclinical gut inflammation. For example, the patient may be at risk of developing SS, either due to one or more symptoms of the disease, an underlying autoimmune disorder, and may present with clinical or subclinical IBD. In these patients, the therapeutic regimen described herein helps to prevent or slow onset or progression of clinical disease. In some embodiments, the method reduces autoantibody titers, including antibody titers associated with SS.

In some embodiments, the patient receives larazotide treatment as an adjunct therapy to immunotherapy or anti-inflammatory treatment. For example, the anti-inflammatory treatment can comprise one or more compounds, including, but not limited to, 4-APAA compounds and 5-ASA compounds (e.g., 4-ASA, 4-Ac APAA, and 4-APAA). As demonstrated herein, such compounds can reduce or prevent cytokine induced tight junction damage that leads to permeability, an activity that may be distinct from their recognized activities of reducing pro-inflammatory cytokine secretion as well as up regulating anti-inflammatory cytokines. In vivo, these anti-inflammatory compounds can reduce or prevent damage to glandular structures through several mechanisms, including prevention of pro-inflammatory cytokine induced damage to the tight junction as well as prevention of cell permeability of glandular structures. Further, the combination therapy with larazotide may result in synergistic reduction in tight junction damage, cell permeability and inflammatory symptoms, including in some embodiments, reduction of symptoms of inflammation associated with SS.

In some embodiments, larazotide or derivative and/or the 4-APAA compounds or 5-ASA compounds are applied locally to affected tissues, such as the skin, eyes, or oral cavity, to reduce lymphocytic infiltration into exocrine glands (e.g., salivary, lacrimal, or sweat glands), reduce pro-inflammatory cytokine mediated damage as well as secretion, and/or restore tight junction integrity. Alternatively, or in addition, the composition is a parenteral composition for systemic administration. Alternatively, or in addition, the composition is an oral formulation to release in the small intestine, including one or more of the duodenum, jejunum, and/or the ileum. In some embodiments, the composition is formulated to release in the large intestine, including one or more of the cecum, the ascending colon, the transverse colon, the descending colon, and/or the sigmoid colon, to improve and/or restore tight junction integrity in the GI.

In accordance with certain embodiments of the invention, larazotide or derivative and/or the 4-APAA compounds or 5-ASA compounds are administered at least once daily to promote and/or restore tight junction integrity of one or more tissues comprising affected exocrine glands, including local application or systemic administration. For example, larazotide or derivative and/or the 4-APAA compounds or 5-ASA compounds may be administered locally or topically from once to ten times daily, such as from once to about five times daily. In various embodiments, the regimen may be for at least about 8 weeks, or at least about 6 months, or more. Alternatively, larazotide (or derivative) and/or the 4-APAA compounds or 5-ASA compounds may be administered systemically and/or to the GI from one to three times daily. In such embodiments, 4-APAA and/or 5-ASA compounds can be administered as an azo-bonded prodrug that is activated by azo reductase in the large intestine.

Other aspects and embodiments of the invention will be apparent from the following detailed description.

BRIEF DESCRIPTION OF THE DRAWINGS

FIG. 1 depicts larazotide acetate's ability to prevent cytokine-induced disruption of tight junctions. PAR-C10 monolayers grown on permeable supports were incubated with IFNγ and TNFα without or with larazotide acetate (1 mM and 5 mM). Each sample was set up in duplicates and TEER was measured at 2 sites in each well. Each bar represents the mean±SEM of TEER readings taken 8 hours apart. Wells not treated with cytokines were used as controls. p values were determined by Kruskal Wallis tests, and adjusted p values by Dunns post-test.

FIG. 3 depicts the ability of 4-Aminosalicylic acid (4-ASA), 4-Amino-phenyl-acetic acid (4-APAA), and 4-Acetyl amino-phenyl-acetic acid (4-Ac APAA) to prevent cytokine-induced disruption of tight junctions. PAR-C10 monolayers grown on permeable supports were incubated with IFNγ and TNFα without or with the aforementioned compounds (5 mM and 10 mM). The compounds were dissolved in dimethyl sulfoxide and added to the culture media to obtain a final concentration of 5 mM and 10 mM each. The TEER values for vehicle controls were 435+64 (mean±SD) and were comparable to the cytokine treated group. Each sample was set up in duplicates and TEER was measured at 2 sites in each well. Each bar represents mean±SEM of TEER readings taken 4 hours apart. Wells not treated with cytokines were used as controls. p values were determined by Kruskal Wallis tests, and adjusted p values by Dunns post-test.

FIG. 4 shows that larazotide acetate can reverse cytokine induced disruption of tight junctions. PAR-C10 monolayers grown on permeable supports were incubated with IFNγ and TNFα for 24 hours. Larazotide acetate (1 mM and 5 mM) was added to the apical surface and the cells allowed to grow for an additional 24 hours. Each sample was set up in duplicates and TEER was measured at 2 sites in each well. Each bar represents mean±SEM of TEER readings taken 8 hours apart. Wells not treated with cytokines were used as controls. p values were determined by Kruskal Wallis tests, and adjusted p values by Dunns post-test.

DETAILED DESCRIPTION

The present invention provides compositions and methods for treating Sjogren's syndrome (SS), including primary or secondary SS, as well as methods for preventing clinical disease in patients at risk of developing clinical SS. In various embodiments, the invention relates to administering a regimen of larazotide (or derivative) and/or 4-APAA compounds or 5-ASA compounds (e.g., 5-ASA, 4-ASA, 4-Ac APAA, and 4-APAA) to a patient in need thereof. In accordance with embodiments of the invention, larazotide and/or the 4-APAA compounds or 5-ASA compounds are applied locally to one or more tissues comprising affected exocrine glands, such as salivary glands, lacrimal glands or ducts, or sweat glands (apocrine or eccrine glands). Further, in some embodiments, routine hygiene or systemic therapy with the compositions described herein promotes and/or restores tight junction integrity of the exocrine glands, leading to reduced inflammation and lymphocyte infiltration.

As demonstrated herein, compounds such as 5-ASA, 4-ASA, 4-Ac APAA, and 4-APAA can reduce or prevent tight junction damage in the presence of cytokines and thereby reducing the permeability, an activity that may be distinct from their recognized activities of reducing pro-inflammatory cytokine secretion and up regulating anti-inflammatory cytokines. In vivo, these anti-inflammatory compounds can reduce or prevent damage to glandular structures through several mechanisms, including prevention of pro-inflammatory cytokine induced damage to the tight junction as well as prevention of cell permeability of glandular structures. Further, the combination therapy with larazotide may result in synergistic reduction in inflammatory symptoms, and tight junction integrity.

Sjogren's syndrome (SS) is an autoimmune condition in which the moisture-producing glands of the body are affected, resulting in the development of, for example, dry mouth (xerostomia), dry eye syndrome (e.g., chronic dry eye and/or xerosis), and/or dry skin (e.g., xerosis), as well as other symptoms. In accordance with embodiments of the invention, the Sjogren's syndrome can be primary Sjogren's syndrome, or may be secondary Sjogren's syndrome, that is, occurring in association with another autoimmune or connective tissue disorder. The inflammation resulting from SS progressively damages glands, and is characterized by lymphocyte infiltration within the glands, elevated levels of B-cell activating factor (BAFF), as well as autoantibody production (e.g., anti-SSA/Ro). See, Nair JJ and Singh TP, *Sjogren's syndrome: Review of the etiology, pathophysiology &potential therapeutic interventions, J. Clin. Exp. Dent.* 2017; 9(4): e584-9.

In various embodiments the patient has or is at risk of developing SS. For example, in some embodiments, the patient does not have a clinical diagnosis of SS, but displays one or more symptoms or markers of the condition, such as dry eye syndrome, dry mouth (e.g., xerostomia), and/or dry skin (e.g., xerosis), and in some embodiments, the presence of at least one other autoimmune condition. In some embodiments, the patient has a clinical diagnosis of SS, including the presence of at least one autoantibody associated with SS (anti-SSA/Ro), or a tissue biopsy demonstrating the infiltration of lymphocytes into glands.

In some embodiments, the larazotide (or derivative) composition and/or 4-APAA compounds or 5-ASA compounds is applied topically to the eye and/or lacrimal glands, for example, as an eye drop, eye wash, or eye lid cleanser. In these embodiments, the larazotide or derivative and/or the 4-APAA compounds or 5-ASA compounds promotes and/or restores integrity of lacrimal gland and duct tight junctions, leading to reduced inflammation and/or lymphocyte infiltration. In some embodiments, the larazotide derivative and/or the 4-APAA compounds or 5-ASA compounds are applied as an eye drop or eye wash, or as a gel or ointment to the eye lid, after routine eye lid cleansing. Larazotide and/or the 4-APAA compounds or 5-ASA compounds may be administered along with a warm compress to the eye (or with excipients) to enhance peptide penetration into glandular structures. Larazotide and/or the 4-APAA compounds or 5-ASA compounds may be administered with excipients for controlled release of the peptide to duct tight junctions. For topical/local administration of 4-APAA compounds or 5-ASA compounds (i.e., when the compounds are not administered to the GI), the compounds will not be administered as an azo-bonded prodrug.

In some embodiments, the larazotide (or derivative) composition and/or the 4-APAA compounds or 5-ASA compounds is/are applied to the oral cavity, e.g., as an aqueous solution or sublingual or buccal composition, to promote and/or restore tight junction integrity of salivary glands, including minor salivary glands that secrete continuously. In these embodiments, the composition is applied as a mouthwash or sublingual treatment, e.g., being held under the tongue to be absorbed into glandular structures. Such compositions may include additional excipients that enhance penetration of the peptide into glandular structures.

In some embodiments, the larazotide (or derivative) composition and/or 4-APAA compounds or 5-ASA compounds is applied to the skin as a solution, gel, cream, ointment, or foam, allowing the peptide agent to be absorbed into affected glands. The topical treatment may be applied after cleansing of the affected area, and/or with a warm compress (or excipients) to enhance peptide penetration into glandular structures.

In some embodiments, larazotide and/or the 4-APAA compounds or 5-ASA compounds is administered systemically, for example, parenterally, to enhance tight junction integrity in various exocrine-containing tissues. In some embodiments, larazotide and/or the 4-APAA compounds or 5-ASA compounds are administered via an intra-nasal route to provide systemic concentrations of the peptide to enhance tight junction integrity in various exocrine-containing tissues.

In some embodiments, the subject displays symptoms of intestinal inflammation, which can be clinical inflammatory bowel disease (IBD) or subclinical gut inflammation. In these embodiments, administration of the larazotide (or derivative) to the GI, or alternatively systemically, can reduce autoantibody production and/or BAFF levels.

The presence of IBD or subclinical intestinal inflammation can be determined, for example, using a variety of tests, including: blood tests for infection, fecal occult blood test, endoscopic procedures (e.g., colonoscopy, flexible sigmoidoscopy, upper endoscopy, capsule endoscopy, double-balloon endoscopy), biopsy, and imaging procedures (X-ray, Computerized tomography (CT) scan, Magnetic Resonance Imaging (MRI), small bowel imaging).

In some embodiments, the patient receives larazotide (or derivative) treatment and/or treatment with 4-APAA compounds or 5-ASA compounds as an adjunct therapy to immunotherapy, such as B-cell depletion, anti-CD20 (e.g., rituximab), or anti-CD22, or other anti-inflammatories as described herein. The combination therapy may result in synergistic reduction in inflammatory or autoimmune symptoms.

The invention involves treatment with larazotide (or derivative) or salt thereof (e.g., acetate salt). Larazotide is a peptide agent that promotes and/or restores tight junction integrity. Larazotide has the amino acid sequence: Gly Gly Val Leu Val Gln Pro Gly (SEQ ID NO: 1), and can be formulated for local application, systemic treatment, or targeted release in desired portions of the GI (e.g., small intestine and/or large intestine). In some embodiments, the larazotide is a derivative, for example, having one or more amino acid substitutions, deletions, and/or insertions (e.g., 1, 2, 3, 4, or 5 amino acid deletions, insertions, and/or substitutions). Larazotide derivatives are described in U.S. Pat. Nos. 8,785,374, 8,957,032, and 9,279,807, which are hereby incorporated by reference in their entirety. In some embodiments, the derivative has one or more non-genetically encoded amino acids, or one or more (or all) D-amino acids. In some embodiments, the larazotide derivative is a prodrug of larazotide or derivative, for example the larazotide has one or more pro moieties at the N-terminus and or C-terminus of the peptide. In some embodiments, pro moiety is a hydrolysable (enzymatically or chemically) group to produce larazotide or derivative in situ.

Larazotide or derivative may be administered in any suitable form, including as a salt. For example, larazotide may be administered as an acetate salt. Salts of larazotide (or derivative), including the acetate salt and hydrochloride salt, are described in US 2013/0281384, which is hereby incorporated by reference in its entirety. Alternative salts may be employed, including any pharmaceutically acceptable salt of the peptide such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

The invention involves treatment with anti-inflammatory compounds, including, but not limited to, 4-APAA compounds or 5-ASA compounds. These compounds promote and/or restore tight junction integrity, particularly in preventing cytokine-induced disruption of tight junctions. The compounds of the present invention can be formulated for local application, systemic treatment, or targeted release in desired portions of the GI (e.g., small intestine and/or large intestine).

In various embodiments, the present invention provides pharmaceutical compositions comprising the larazotide or derivative and/or the 4-APAA compounds or 5-ASA compounds (e.g., 5-ASA, 4-ASA, 4-Ac APAA, and 4-APAA) in various formulations. Any pharmaceutical composition described herein can take the form of tablets, pills, pellets, capsules, capsules containing liquids, capsules containing multiparticulates, powders, solutions, gels, lotions, emulsion, eye drops, eyewash, suppositories, emulsions, aerosols, sprays, suspensions, delayed-release formulations, sustained-release formulations, controlled-release formulations, or any other form suitable for use.

In various embodiments, the pharmaceutical compositions are formulated as a composition adapted for a mode of administration selected from eye drop, eyewash, topical, sublingual, buccal, mouthwash, parenteral, oral, intra-nasal or rectal.

In some embodiments, the pharmaceutical compositions are formulated as a composition adapted for parenteral administration. Dosage forms suitable for parenteral administration (e.g. intravenous, intramuscular, intraperitoneal injection, infusion, and subcutaneous) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In some embodiments, the compositions may additionally include pharmaceutically acceptable excipients or carriers. Exemplary excipients include sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpolypyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., mucoadhesive agents such as glycoproteins or derivatives and mixtures of such excipients. One of skill in the art will recognize that particular excipients may have two or more functions.

Various methods may be used to formulate and/or deliver the larazotide or derivative to a gastrointestinal location of interest. For example, the compositions described herein may be formulated for targeted delivery to the gastrointestinal tract including the stomach, small intestine, large intestine and rectum including all subsections thereof. By targeting release of the peptide agent in the affected region(s) (e.g. duodenum, jejunum and ileum, colon *transversum*, colon *descendens*, colon *ascendens*, colon sigmoidenum and cecum), tight junction integrity at any portion of the GI can be improved and/or restored, including in some embodiments, in severely damaged tissue.

In some embodiments, the composition is formulated to release in the small intestine, including one or more of the duodenum, jejunum, and/or the ileum. In some embodiments, the composition is formulated to release in the large intestine, including one or more of the cecum, the ascending colon, the transverse colon, the descending colon, and/or the sigmoid colon. In some embodiments, the composition dissolves in the stomach. In other embodiments, the composition is formulated so as to not substantially release in the stomach.

In various embodiments, the composition may be formulated to have sustained-release profiles, i.e. slow release of the larazotide or derivative in the body (e.g., GI tract) over an extended period of time. In various embodiments, the composition may be formulated to have a delayed-release profile, i.e. not immediately release the larazotide or derivative upon ingestion; rather, postponement of the release until the composition is lower in the gastrointestinal tract; for example, for release in the small intestine (e.g., one or more of duodenum, jejunum, ileum) and/or the large intestine (e.g., one or more of cecum, ascending, transverse, descending or sigmoid portions of the colon, and rectum). In an embodiment, the pharmaceutical composition is formulated to have a delayed-release profile as described in, for example, U.S. Pat. No. 8,168,594, the entire contents of which are hereby incorporated by reference. In some embodiments, an effective amount of larazotide is released in the ileum to reduce antigenic display to the immune system. In some embodiments, the compositions are formulated to have both pH sensitive delayed release and time sensitive controlled release function.

In various embodiments, the compositions of the present invention may use one or more modified-release coatings such as delayed-release coatings to provide for effective, delayed, yet substantial, delivery of the peptide to the GI tract. For example, a composition can be enteric coated to delay release of the peptide until it reaches the small intestine or the large intestine. Compositions may be pH-dependent or pH-independent or pH-dependent and time-dependent. In various embodiments, the compositions of the present invention may use one or more modified-release functions such as pH sensitive delayed-release coatings and controlled release function to provide for effective, delayed and timed, yet substantial, delivery of the peptide to the GI tract. For example, a composition can be enteric coated to delay release of the peptide until it reaches the small intestine or the large intestine and have a function to slowly or rapidly release the peptide after reaching the small intestine or large intestine.

For example, the larazotide or derivative and/or the 4-APAA compounds or 5-ASA compounds may be administered to the duodenum of the patient, as an oral dosage, delayed-release composition that contains peptide coated-coated beads that are stable in gastric fluid and unstable in intestinal fluid so as to substantially release the peptide in the duodenum. In these embodiments, the 4-APAA compounds or 5-ASA compounds may be azo-bonded compounds as described herein. In these or other embodiments, the composition may comprise a population of beads with a pH-dependent coating to affect release of the peptide in the jejunum of the patient. In these or other embodiments, the composition may comprise a population of beads with a pH-dependent coating to affect release of the peptide in the ileum of the patient. In some embodiments, the composition comprises 2 or 3 populations of coated beads, to provide release of the peptide in at least two regions of the small intestines. The oral dosage composition can be in the form of a capsule or tablet. The pH-dependent coating in some embodiments is a 1:1 co-polymer of methacrylic acid and ethyl acrylate, wherein the thickness of the layer determines the release profile of each bead. The beads may have one or more additional coatings such as a base coat, a separating layer, and an overcoat layer.

In some embodiments, delayed release oral dosage bead compositions contain a peptide encaptured in a pH-dependent matrix that is stable in gastric fluid and unstable in intestinal fluid so as to substantially release the peptide in the small intestine or large intestine. The pH-dependent matrix in some embodiments is a mixture of co-polymer of methylacrylic acid and ethyl acrylate, wherein the ratio of these polymers determines the release profile of each bead.

In an exemplary oral dosage composition, an effective amount of larazotide or derivative (e.g., as the acetate salt) and/or the 4-APAA compounds or 5-ASA compounds is provided in at least two of: a first delayed-release particle that is capable of releasing the peptide in the duodenum of a patient, a second delayed release particles that is capable of releasing the peptide in the jejunum of a patient, a third delayed release particle that is capable of releasing the peptide in the ileum of a patient. Each particle may have a core particle, a coat comprising larazotide or derivative over the core particle, and a delayed-release coating (e.g., a 1:1 co-polymer of acrylate and methacrylate) outside the coat comprising larazotide or derivative. The first delayed-release particles release at least 70% of the peptide in the first delayed-release particles by about 60 minutes of exposure to simulated intestinal fluid having a pH of greater than 5; the second delayed-release particles release at least 70% of the peptide by about 30 and about 90 minutes of exposure to simulated intestinal fluid having a pH of greater than 5; and the third delayed release particles release at least 70% of the peptide in the third delayed release particles between about 90 and about 180 minutes (e.g., between about 90 and about 150 minutes) of exposure to simulated intestinal fluid having a pH greater than 5.

In another embodiment, larazotide and/or the 4-APAA compounds or 5-ASA compounds are formulated in a vehicle for local administration to oral mucosa. In an exemplary embodiment, an oral mucosa delivery composition comprises an effective amount of larazotide or larazotide derivative that is provided in a mucoadhesive tablet, which allows for buccal adhesion in the oral mucosa. An oral mucosa delivery composition may contain a hydrogel forming property with a mucoadhesive component and a solubility promoter. For example, hydrogel can promote maximum spread of the drug over the surface of a mucosal membrane and the mucoadhesive component can promote retention of the dosage at the mucosal site by locking the drug in place. Such formulations may be designed to provide a range of delivery rates controlled by diffusion.

In some embodiments, larazotide and/or the 4-APAA compounds or 5-ASA compounds are formulated in a vehicle for topical administration to the eye. Such ophthalmic compositions can include, without limitation, saline, which may include a pH buffering agent (e.g., phosphate-buffered saline). In some embodiments, the vehicle comprises a tonicity agent, and the composition can be isotonic or hypotonic with respect to natural tears. Tonicity agents include sodium chloride, potassium chloride, magnesium chloride, calcium chloride, dextrose and/or mannitol, which may be added to the composition to approximate physiological tonicity. In general, the compositions will have a tonicity agent in an amount sufficient to cause the final composition to have an acceptable osmolality. For example, for an ophthalmic composition, the composition may be in the range of about 100 to 500 mOsm. The composition may employ an appropriate buffer system or pH adjuster, such as, those selected from sodium phosphates, potassium phosphates, sodium borate, sodium carbonate, boric acid, and phosphoric acid.

The dose of larazotide or derivative administered may depend on the route of administration and/or the form of the composition. For example, peptide (or salt thereof) can be administered at from about 0.1 mg to about 10 mg per dose, or at from about 0.1 mg to about 5 mg, or at from about 0.1 mg to about 2 mg, or at from about 0.1 mg to about 1 mg per dose. In some embodiments, larazotide or derivative is administered at from about 1 mg to about 25 mg per day, in a plurality of subdoses.

In accordance with certain embodiments of the invention, larazotide or derivative and/or the 4-APAA compounds or 5-ASA compounds are administered more than once daily to promote and/or restore tight junction integrity. For example, larazotide or derivative and/or the 4-APAA compounds or 5-ASA compounds may be administered from once to ten times daily by topical or local application, or from once to about five times daily, such as about two times daily, about three times daily, about four times daily, or about five times daily. Alternatively, or in addition, the larazotide or derivative and/or the 4-APAA compounds or 5-ASA compounds are administered systemically once or twice daily. Alternatively, or in addition, the larazotide or derivative and/or the 4-APAA compounds or 5-ASA compounds are administered to the GI (optionally as azo-bonded prodrug) from one to three times daily.

In various embodiments, the larazotide regimen is for at least one week, or for at least one month. The regimen in some embodiments is intermittent to reduce symptoms as they occur, or is a chronic regimen manage the condition. In some embodiments, the larazotide or derivative may be administered for a prolonged period (e.g., chronically). For example, the regimen may be for at least about 8 weeks, at least about 9 weeks, at least about 10 weeks, at least about 11 weeks, or at least about 12 weeks. In some embodiments, the regimen is for at least about 1 month, at least about 6 months, or at least about 12 months. In some embodiments, the regimen is for about 1 year or more.

In some embodiments, the patient may receive adjunct therapy, which in some embodiments is synergistic with larazotide (or derivative) treatment. In some embodiments, the additional therapeutic agent is an anti-inflammatory agent such as steroidal anti-inflammatory agents or non-steroidal anti-inflammatory agents (NSAIDs). Steroids, particularly the adrenal corticosteroids and their synthetic analogues, are well known in the art. Examples of corticosteroids include, without limitation, hydroxyltriamcinolone, alpha-methyl dexamethasone, beta-methyl betamethasone, beclomethasone dipropionate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometholone, fluperolone, fluprednisolone, hydrocortisone, meprednisone, paramethasone, prednisolone, prednisone, and budesonide. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, larazotide (or derivative) is administered to a patient undergoing treatment with mesalamine (5-aminosalicylic acid), to reduce inflammation in the GI, which can be synergistic with larazotide (or derivative) treatment.

In an embodiment, the additional therapeutic agent is an immunosuppressive agent such as azathioprine, cyclosporin, infliximab, and alemtuzumab.

In some embodiments, the additional agent is immunotherapy, for example, anti-CD20 (e.g., rituximab), or anti-CD22.

In some embodiments, the additional therapeutic agent is an immunomodulating agent such as 5-Aminosalicylic acid (5-ASA), 4-Aminosalicylic acid (4-ASA), 4-acetylamino phenyl acetic acid (4-Ac APAA) or 4-aminophenylacetic acid (4-APAA).

In some embodiments involving administration to the GI, the additional therapeutic agent is a combination of an anti-inflammatory agent or immunomodulating agents connected by a diazo bond, such as 5-aminosalicylic acid (5-ASA) azo bonded 4-aminophenylacetic acid (4-APAA).

U.S. Pat. Nos. 6,903,082, 7,425,578, and 8,048,924, which are hereby incorporated by reference in their entireties, describe methods and compositions for the treatment of inflammatory conditions of the gastrointestinal tract in which 5-ASA compounds are conjugated via an azo bond to 4-aminophenylacetic acid (4-APAA) compounds. The azo bond can be cleaved by enzymes secreted by bacteria in the lower gastrointestinal tract, yielding pharmaceutically active 5-ASA and 4-APAA compounds.

In some embodiments, the agent is a compound of the formula:

where $R^1$, $R^2$, and $R^3$ are independently hydrogen, halogen, or C1 to C4 alkyl, and $R^4$ is:

where $R^5$ is selected from hydrogen, halogen, and C1 to C4 alkyl; or $R^4$ is:

where $R^6$, $R^7$, and $R^8$ are independently hydrogen, halogen, or C1 to C4 alkyl. For example, in some embodiments, the compound is a 4-aminophenylacetic acid azo bonded dimer.

In some embodiments, the compound is 5-(4-carboxymethyl-phenylazo)-2-hydroxy-benzoic acid.

The term "4-APAA compounds" as used herein includes 4-aminophenylacetic acid and related compounds, for example, 4-aminophenylacetic acid (4-APAA):

as well as (4-acetylaminophenyl)-acetic acid (actarit):

and other 4-aminophenylacetic acid derivates.

The term "5-ASA compounds" as used herein include 5-aminosalicylic acid (mesalamine) and related compounds, and compounds that react under physiological conditions to form or release 5-ASA and related compounds.

The term "4-APAA azo compounds" as used herein includes compounds that react under physiological conditions to form or release 4-APAA and related compounds in the GI. 4-APAA azo compounds include, for example, 4-aminophenylacetic acid azo bonded dimer [4-(4-carboxymethyl-phenylazo)-phenyl]-acetic acid:

In some embodiments, the 4-APAA compound is INN-108, 5-(4-carboxymethyl-phenylazo)-2-hydroxybenzoic acid:

The term "related compounds" as used herein includes analogs, derivatives, and compounds comprising the basic structural feature that are responsible for a compound's therapeutic activity.

For all compounds described herein, the invention includes the esters or pharmaceutically acceptable salts of the compounds.

Other aspects and embodiments of the invention will be apparent to one of ordinary skill in the art in view of the present disclosure and from the following examples.

EXAMPLES

Example 1: Larazotide Acetate and Other Anti-Inflammatory Compounds Prevent Cytokine-Mediated Disruptions of Tight Junctions in Salivary Gland Epithelial Cells The purpose of this experiment was to evaluate whether larazotide acetate and other anti-inflammatory compounds could prevent cytokine-mediated tight junctional disruption in a salivary gland epithelial cell model that mimics the dysfunction exhibited in Sjögren's syndrome.

Specifically, an in vitro assay system to measure tight junction integrity was established using PAR-C10 cells, an immortalized rat acinar epithelial cell line, which mimic the biochemical and functional characteristics of primary salivary gland acinar cells. PAR-C10 cells form a monolayer of cuboidal cells, and are attached to each other with well-formed junctional complexes. PAR-C10 cells have been used to model the effect of inflammatory cytokines on tight junctions in vitro. Quissell et al., (1998) *In Vitro Cell. Dev. Biol. Anim.* 34: 58-67; Baker et al., *Am. J. Cell Physiol.* 295:C1191-1201. The cells were seeded on permeable supports in 12 well plates and cultured to form monolayers. The trans-epithelial electrical resistance (TEER) across the epithelial monolayer was measured to evaluate formation of tight junction between the cells. Three ng/ml of each pro-inflammatory cytokines, interferon gamma (IFNγ) and tumor necrosis factor alpha (TNFα) were added to the monolayers and incubated for 24 hours in order to cause tight junction disruption. Larazotide acetate (1 mM and 5 mM) or any one of 4-Aminosalicylic acid (4-ASA), 4-Amino-phenyl-acetic acid (4-APAA), and 4-Acetyl amino-phenyl-acetic acid (4-Ac APAA) (5 or 10 mM) of was added to the apical surface and the cells allowed to grow for an additional 24 hours. The compounds were dissolved in dimethyl sulfoxide and added to the culture media to obtain a final concentration of 5 mM and 10 mM each.

TEER measurements were used to determine the effect of larazotide acetate (1 or 5 mM) and other anti-inflammatory compounds (4-Aminosalicylic acid (4-ASA), 4-Amino-phenyl-acetic acid (4-APAA), and 4-Acetyl amino-phenyl-acetic acid (4-Ac APAA)) (5 or 10 mM) on tight junctions, in the presence of cytokines. To determine a therapeutic effect, the cells were pre-treated with cytokines, and the ability of larazotide acetate (1 or 5 mM) or 4-ASA, 4-APAA, and 4-Ac APAA (each at 5 or 10 mM) to reverse junctional disruption was evaluated. Wells not treated with cytokines were used as controls. p values were determined by Kruskal Wallis tests, and adjusted p values were determined by Dunns post test.

Figure 1:
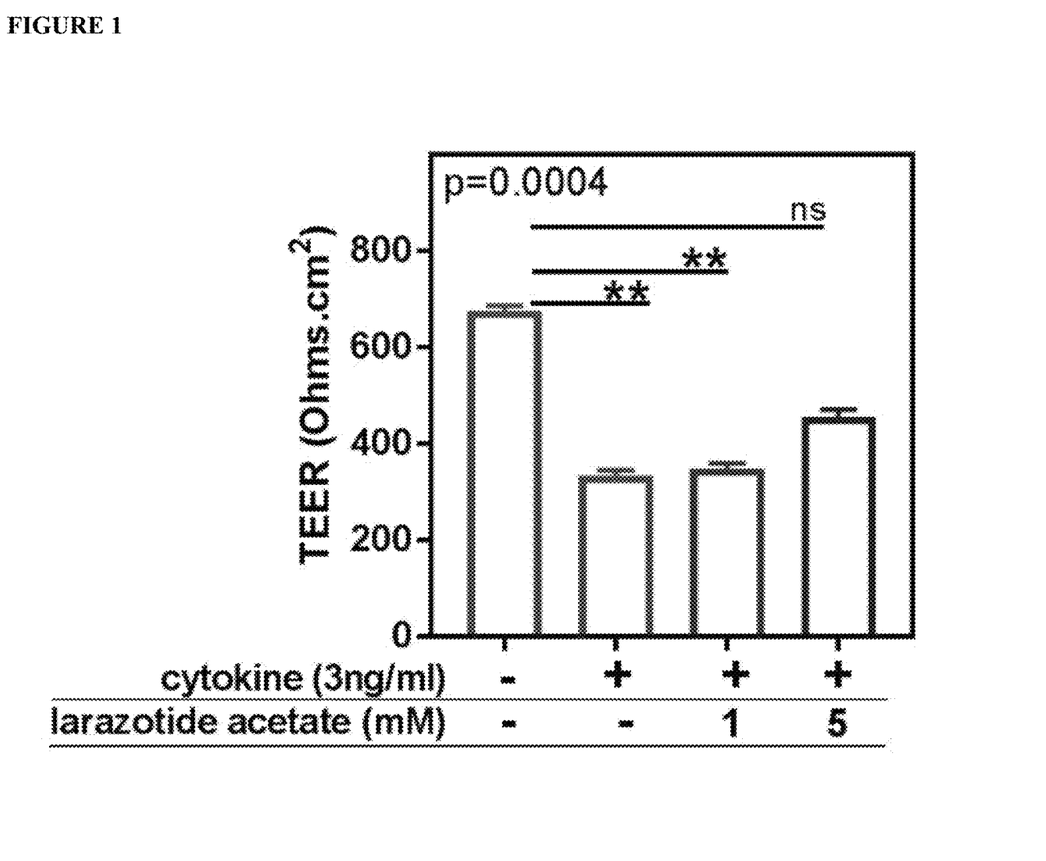
Figure 2:
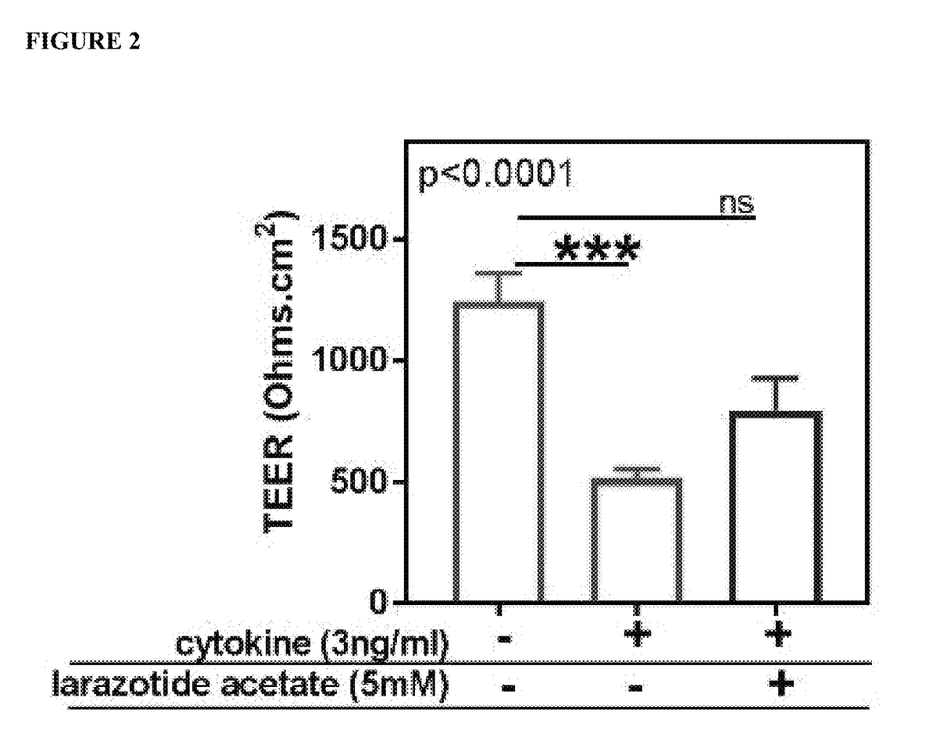
FIG. 2 shows that larazotide acetate at 5 mM concentration can reproducibly prevent cytokine induced disruption of tight junctions. Each bar represents the mean±SEM of TEER readings taken 4 hours apart from 2 independent experiments. Wells not treated with cytokines were used as controls.
Figure 3:
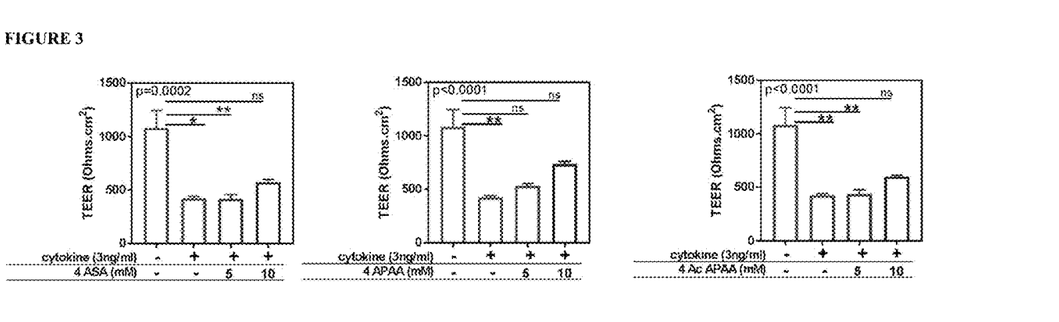
Figure 4:
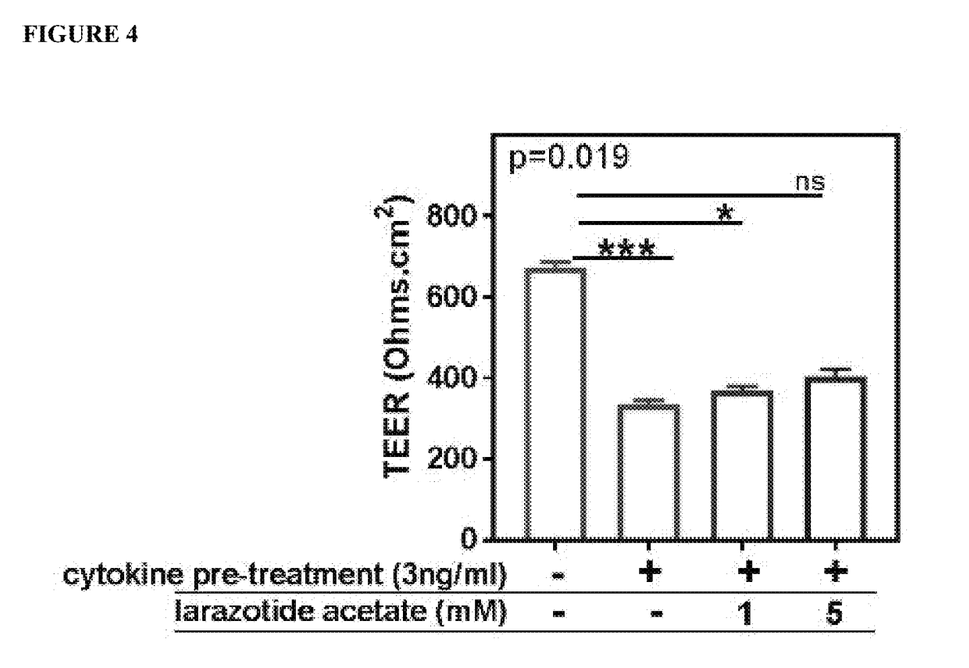

The results of the experiment found that, in culture, the cells formed a monolayer of cuboidal cells and showed a gradual increase in TEER over time, indicating the formation of junctional complexes. However, addition of IFNγ and TNFα resulted in a drop in TEER after 18-20 hours of incubation. Co-incubation of larazotide acetate (FIG. 1 and FIG. 2), 4-Aminosalicylic acid, 4-Amino-phenyl-acetic acid, and 4-Acetyl amino-phenyl-acetic acid (FIG. 3) with cytokines was each able to significantly prevent a drop in TEER. Further, larazotide acetate was able to reverse the cytokine-mediated drop in TEER (FIG. 4).

Larazotide acetate and/or other anti-inflammatory compounds (e.g., 4-ASA, 4-APAA, and 4-Ac APAA) show promise in preventing cytokine mediated tight junctional disruption in salivary gland acinar cells. Further, larazotide acetate also reversed cytokine induced tight junction disruptions in in vitro experiments and can be a promising drug to treat salivary gland dysfunction in Sjögren's syndrome.

---

---

The invention claimed is:

1. A method for treating dry eye syndrome associated with Sjogren's syndrome, comprising administering a regimen of larazotide or larazotide derivative comprising the amino acid sequence of SEQ ID NO: 1 with one or more D amino acids to a subject having Sjogren's syndrome, wherein the regimen comprises administering the larazotide or larazotide derivative topically to the subject's eye.

2. The method of claim 1, further comprising administering a 5-Aminosalicylic acid (5-ASA) compound, a 4-Aminosalicylic acid (4-ASA) compound, a 4-acetylamino phenyl acetic acid (4-acetyl APAA) compound and/or a 4-aminophenylacetic acid (4-APAA) compound topically to the subject's eye.

3. The method of claim 2, wherein 4-APAA or 4-acetyl APAA is administered.

4. The method of claim 1, wherein the subject has primary or secondary Sjogren's syndrome.

5. The method of claim 1, wherein the larazotide regimen comprises administering the larazotide or larazotide derivative topically to the eye from 1 to 5 times per day.

6. The method of claim 5, wherein the regimen is for at least one week or for at least one month.

7. The method of claim 5, wherein the regimen is intermittent to reduce symptoms, or is a chronic regimen.

8. The method of claim 1, wherein the larazotide is larazotide acetate.

9. The method of claim 1, wherein the subject is undergoing treatment with an anti-inflammatory agent.

10. The method of claim 1, wherein the subject is undergoing immunotherapy.

\* \* \* \* \*

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide.

<400> SEQUENCE: 1

Gly Gly Val Leu Val Gln Pro Gly
1               5